United States Patent [19]

Smith et al.

[11] Patent Number: 6,103,526
[45] Date of Patent: Aug. 15, 2000

[54] *SPODOPTERA FRUGIPERDA* SINGLE CELL SUSPENSION CELL LINE IN SERUM-FREE MEDIA, METHODS OF PRODUCING AND USING

[75] Inventors: Gale E. Smith, Wallingford; Harald G. Foellmer, Guilford; John Knell, Meriden, all of Conn.; James DeBartolomeis, Millbury, Mass.; Andrei I. Voznesensky, West Hartford, Conn.

[73] Assignee: Protein Sciences Corporation, Meriden, Conn.

[21] Appl. No.: 09/169,178

[22] Filed: Oct. 8, 1998

[51] Int. Cl.⁷ ........................................... C12N 5/00
[52] U.S. Cl. ........................... 435/348; 435/384; 435/387
[58] Field of Search ..................................... 435/348, 384, 435/387

[56] References Cited

PUBLICATIONS

Hink and Butz. In Vitro Cellular & Developmental Biology. 21(6). pp. 333–339, Jun. 1985.

*Primary Examiner*—Leon B. Lankford, Jr.
*Attorney, Agent, or Firm*—Frommer Lawrence & Haug LLP; Thomas J. Kowalski

[57] ABSTRACT

Disclosed and claimed is a new insect cell line, Sf900+, ATCC CRL-12579. The insect cell line was established from Lepidoptera, Noctuidae, *Spodoptera frugiperda* Sf-9 (ATCC CRL-1771) through multiple rounds of limiting dilution and selection in a serum-free insect medium supplemented with added human insulin. The insect cell line is useful in BEVS or as an adjuvant and has many characteristics and advantages. Also disclosed and claimed are recombinant proteins from recombinant baculovirus expression in insect cells such as Sf900+ cells, for instance, HA, NA, EPO, CD4, CEA, and thrombospondin.

16 Claims, 3 Drawing Sheets

SPODOPTERA FRUGIPERDA SINGLE CELL SUSPENSION CELL LINE IN SERUM-FREE MEDIA, METHODS OF PRODUCING AND USING

RELATED APPLICATIONS

Reference is made to U.S. application Ser. Nos. 08/965,698, filed Nov. 7, 1997; 08/120,601, filed Sep. 13, 1993, 08/453,848, filed May 30, 1995, now U.S. Pat. No. 5,858,368 09/111,169, filed Jul. 7, 1998, 08/850,366, filed May 2, 1997 now abandoned, and 08/430,971, filed Apr. 28, 1997 now U.S. Pat. No. 5,976,552 each of which is hereby incorporated herein by reference. Similarly, all documents cited in the foregoing referenced applications and patent are hereby incorporated herein by reference. In addition, documents cited in the following text and documents referenced in documents cited in the following text are likewise incorporated herein by reference.

FIELD OF THE INVENTION

The present invention relates to a continuous insect cell line that grows as a single cell suspension in a culture media that is free of serum. Specifically, the cells are self-renewing; grow in suspension as single cells; replicate in a serum-free medium; are stable and can be propagated continuously for at least 6 months and 50 passages; are free of any detectable adventitious agents including mycoplasma, spiroplasma, and viruses, including retroviruses; support the replication of baculoviruses and produce high titers of virus; and produce foreign gene products for use in human and animal health applications.

BACKGROUND OF THE INVENTION

Insect cells that support the replication of baculoviruses were of interest initially for the study of the basic biology of insect viruses and in agricultural use of baculoviruses for microbial pest control applications. Hink (Nature, 226:466–467, 1970) reported the first continuous insect (Lepidoptera) cells that were shown to support the replication of baculoviruses. Faulkner and Henderson (Virology, 50:920–924, 1972) demonstrated that baculoviruses could be continuously propagated in a stable insect cell line. More recently, with the development of baculovirus expression vector systems, the need for insect cells that can be used for the commercial production of human and animal health and diagnostic products has become important.

Commonly used expression systems for the production of recombinant DNA products are bacterial, yeast, insect and mammalian cells, and transgenic animals. The general method is to introduce foreign genes into the cells or organisms creating a transformed cell line or transgenic organism, which are unique for each gene product. However, in the baculovirus expression system, foreign genes are cloned into individual baculovirus vectors and a single insect cell line, susceptible to baculovirus infection, can be used to produce an unlimited number of foreign gene products.

The ideal insect cell line for use with baculovirus expression vectors would replicate continuously in suspension as single cells making them ideal for use in large-scale pharmaceutical bioreactors. The insect cells should also grow to high density with a high degree of viability in a low-cost, serum-free medium and support the replication of baculoviruses to high titers. The ideal insect cell line when infected with a genetically engineered recombinant baculovirus would produce gene products at high levels and produce those products consistently over many passages. The ideal insect cell for the production of pharmaceutical products from baculovirus expression vectors would also meet all regulatory requirements for identity and safety and be readily expandable to large-scale bioreactors for the manufacture of pharmaceutical products. Finally, due to the high cost of serum and the potential for contamination with adventitious agents such as Bovine spongiform encephalopathy, a chronic degenerative disease affecting the central nervous system of cattle (mad cow disease), the ideal insect cell line would be stored and cultured in a serum-free medium. To date, no such insect cell line with these ideal properties has been described. The current invention has as an objective to provide an insect cell line, preferably such a cell line with any or all of these ideal properties.

Baculoviruses are widely used for foreign gene expression in insect cells (see, e.g., Smith, et al., U.S. Pat. No. 4,745,051 (recombinant baculovirus) and U.S. Pat. No. 4,879,236; Summers and Smith. A Manual of Methods for Baculovirus Vectors and Insect Cell Culture Procedures, May 1987, Texas A&M University; O'Reilly et al. Baculovirus Expression Vectors A Laboratory Manual, 1994, Oxford University Press; and references therein).

In particular, baculoviruses such as *Autographa californica* nuclear polyhedrosis virus (AcNPV) are grown in established Lepidoptera insect cell lines including ones derived from ovarian tissue of the fall armyworm (*Spodoptera frugiperda*) and the cabbage looper (*Trichoplusia ni*) and midgut tissue from *T. ni*. The cell lines in most common use to support AcNPV replication and production of recombinant products are *S. frugiperda* IPLB-SF-21 (Vaughn, et al. In Vitro 13:213–217, 1977) and *S. frugiperda* Sf-9 cells (Summers and Smith, supra), *T. ni* TN-368 cells (Hink, Ibid. 1970) and *T. ni* BTI-TN-5-B1-4 cells (Granados, U.S. Pat. Nos. 5,300,435, 5,298,418). The Sf-9 (ATCC CRL-1771) and BTI-TN-5-B1-4 (ATC, CRL 10859) cells were cloned in medium containing 10% or 8% Fetal Bovine Serum, respectively. These and other insect cells can be adapted to commercial serum-free medium, such as Sf-900 II SFM (Life Technologies, Grand Island, N.Y. 14072), using procedures known to those skilled in the art. Adapting cells repeatedly for use in the manufacture of pharmaceutical products is not desirable in that it is time consuming, may result in cells with differing properties with each adaptation, and the adapted culture of cells would contain a variable level of residual serum.

In addition, the BTI-TN-5-B1-4 cells severely clump in suspension with serum-free medium reducing its effectiveness as a host cell for foreign gene productions with baculovirus vectors. The use of non-carboxylated sulfated polyanions may help in overcoming this problem (Shuler and Dee, U.S. Pat. No. 5,728,580, Mar. 17, 1998). However, sulfated polyanions can block the infection of the cells with baculoviruses, thus complicating their use in the manufacture of recombinant DNA gene products.

Insulin is an anabolic peptide hormone important in the regulation of glucose metabolism. Insect and mammalian cells follow similar patterns of glucose metabolism from glucose to pyruvic acid; therefore it is not surprising that insulin-like peptides are produced in insects. The insect prothoracicotrophic hormone (PTTH) activates the prothoracic glands to produce the molting hormone ecdysone. The PTTH bombyxin from the silkmoth *Bombyx mori* has 40% homology with human insulin. Bombyxin binds to specific receptors and induces morphological changes in a *B. mori* cell line, specifically increasing cell size 1–2 weeks after exposure to a low concentration of bombyxin (Tanaka, M. et al., Regul. Pept. 57(3):311–318, 1995). *S. frugiperda* Sf9 cells have receptors for the insulin-like peptide hormone bombyxin and *B. mori* bombyxin binds with high affinity to receptors on *S. frugiperda* cells with a dissociation constant of about 0.26 nM (Fillbright, et al., Eur. J. Biochem. 245(3):774–780, 1997). Although insulin is commonly used in growth media for mammalian cells, it has not been described for use in media for insect cells. Goodwin and Adams (Ed. Kurstak, Maramorosch, Dubendorfer, Invertebrate Systems In Vitro, Elsevier/North-Holland Biomedical Press, 443–509, 1980) reported that 35 units/L of insulin did not affect the growth of *Lymantria dispar* insect cells. In the present invention insulin-containing serum-free medium was used in the generation of a new *S. frugiperda* cell line.

Reference is also made to U.S. Pat. Nos. 4,072,565, 5,135,866, 5,532,156, and 5,024,947. Inslow et al., U.S. Pat. No. 5,024,947 relates to a serum-free media for growth on insect cells and expansion of products thereby, and either individually or in any combination fails to teach or suggest the insect cell line or the methods of making or using it of the present invention. Talbot et al., U.S. Pat. Nos. 5,532,156 is directed to a hepatocyte cell line derived from the epiblast of pig blastocysts and similarly either individually or in any combination fails to teach or suggest the insect cell line or the methods of making or using it of the present invention. Heifetz et al., U.S. Pat. No. 5,135,866 provides a very low protein nutrient medium for cell culture and likewise either individually or in any combination fails to teach or suggest the insect cell line or the methods of making or using it of the present invention. And, Weiss et al., U.S. Pat. No. 4,072,565 relates to the production of viruses in tissue culture without the use of serum, and either individually or in any combination fails to teach or suggest the insect cell line or the methods of making or using it in the present invention.

Thus, it is believed that heretofore, a cell line as described and claimed herein, as well as the methods for making and using such a cell line, have not been disclosed or suggested in the art.

OBJECTS AND SUMMARY OF THE INVENTION

It is an object of the invention to provide an insect cell line.

It is a further object of the invention to provide such a cell line that has one or all of the following characteristics: replicate continuously in suspension as single cells, making them ideal for use in large-scale pharmaceutical bioreactors; grow to high density with a high degree of viability in a low-cost, serum-free medium; support the replication of baculoviruses to high titers; when infected with a genetically engineered recombinant baculovirus produce gene products at high levels and produce those products consistently over many passages; meet all regulatory requirements for identity and safety and be readily expandable to large-scale bioreactors for the manufacture of pharmaceutical products; and, able to be stored and cultured in a serum-free medium. Indeed, it is another object of the invention to provide an insect cell line having all of these characteristics.

Yet another object of the invention is to provide an insect cell line which overcome problems of prior insect cell lines, e.g., problems identified herein with prior insect cell lines.

It has surprisingly been found that a new insect cell line evolved or was derived from *Spodoptera frugiperda* Sf-9 cells in a serum-free medium containing added insulin. The new cell line, designated Sf900+ cells, have a phenotype and genotype unique from the parent Sf-9 cells. Further, it has surprisingly been found that the new cell line has the properties that make them ideal for use in the large-scale production of gene products for use in human and animal health. The cells grow continuously as single cell suspensions in a commercial serum-free medium, divide rapidly and maintain a high level of viability, and are highly permissive for infection with baculoviruses producing high virus titers and high levels of recombinant gene products. In addition, the Sf900+ cells meet the requirements for identity and safety recommended for the manufacture of recombinant DNA gene products under the U.S. current Good Manufacturing Practices (cGMP) specifications (Code of Federal Regulations 21, Part 211, Current Good Manufacturing Practice for Finished Pharmaceuticals, Apr. 1, 1995). The Sf900+ cells are also in compliance with the guidelines issued by the U.S. Food and Drug Administration Points to Consider for Cell Lines used in the Production of Pharmaceutical Products (Points to Consider in the Characterization of Cell Lines Used to Produce Biologicals, issued May 17, 1993, U.S. Food and Drug Administration, Rockville, Md.).

In one embodiment of this invention provides a new cell line that replicates as a single cell suspension and is stable for 50 or more passages in serum-free media.

Another embodiment of this invention provides a method to use the new cell line for the production of high titers of wild-type and genetically engineered recombinant baculoviruses.

Yet another embodiment of this invention provides the use of the cell line to make baculovirus expression vectors and to produce high-titer stocks of recombinant virus suitable for use in the production of recombinant gene products.

Still another embodiment of this invention provides the new cell line as conforming to standard tests for identity and safety, whereby the new cell line can be used in the commercial manufacture of pharmaceutical products.

And, another embodiment of this invention provides the use of the new cell line for large-scale commercial production of recombinant gene products from baculovirus expression vectors.

The inventive cell line is especially suited for practicing the teachings of the applications and patent above-referenced under "Related Applications"; and, this provides yet a further embodiment of the invention.

Further embodiments of this invention will be set forth in the description that follows, and will become apparent to those skilled in the art and as learned by the practice of the invention.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which.

DETAILED DESCRIPTION

Figure 1:
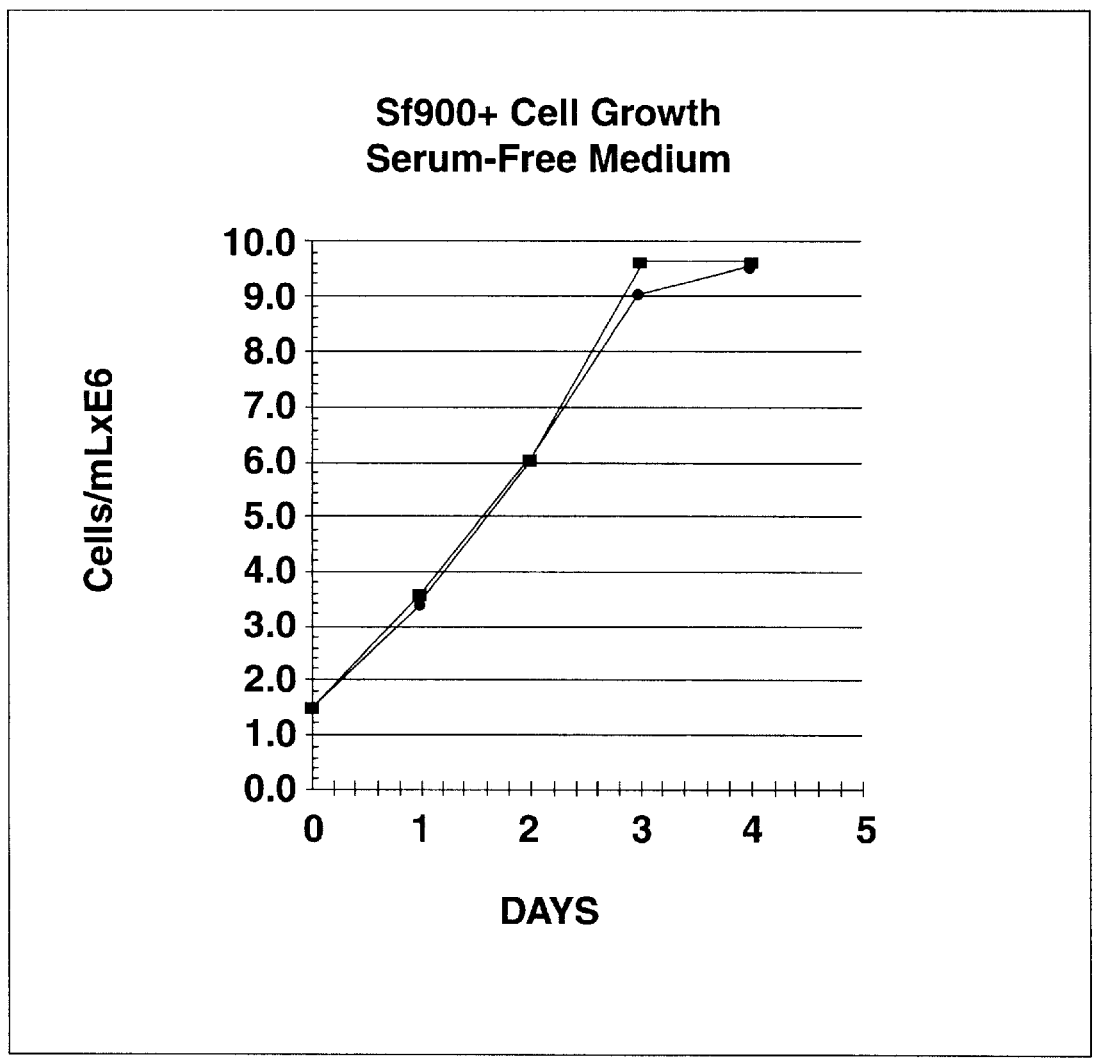
FIG. 1 shows two typical growth curves of Sf900+ cells in serum-free medium (Sf900+ cells were diluted into culture medium to $1.5 \times 10^6$ cell/ml and the growth of the cells monitored every 24 hours for 4 days. Over the first 3 days the cells doubled approximately every 22–24 hours to 9.0 and $9.6 \times 10^6$ cell/ml and over 98% of the cells remained viable. On the $4^{th}$ day, cell growth was minimal and the viability dropped to approximately 95%)

The generation and use of recombinant baculovirus is known; for instance, from documents cited herein, including the above-referenced applications and patent.

Insect cells from *S. frugiperda* and other Lepidopteran insect species have been described in the literature and there general use to support the infection and replication of baculoviruses and the production of recombinant proteins is well known (see, e.g., Smith et al., U.S. Pat. No. 4,745,051 (recombinant baculovirus); Richardson, C. D. (Editor), *Methods in Molecular Biology* 39, "Baculovirus Expression Protocols" Humana Press Inc. (1995)); Smith et al., "Production of Human Beta Interferon in Insect Cells Infected with a Baculovirus Expression Vector," Mol. Cell. Biol., 3(12):2156–2165 (1983); Pennock et al., "Strong and Regulated Expression of *Escherichia coli* B-Galactosidase in Insect Cells with a Baculovirus vector," Mol. Cell. Biol., 4(3):399–406. (1984); EPA 0 370 573, U.S. application Ser. No. 920,197, filed Oct. 16, 1986, EP Patent publication No. 265785). However, while *S. frugiperda* and other Lepidopteran insect species have been described in the literature, the literature fails to teach or suggest the insect cell line of the present invention. Nonetheless, the insect cell line of the present invention can be used instead of previously-described *S. frugiperda* and other Lepidopteran insect species, for instance, to support the infection and replication of baculoviruses and the production of recombinant proteins.

The expression of antigens in insect cells with baculovirus expression vectors and their potential as vaccines is also well known. For example, Kamiya et al., Virus Res. 32:375–379 (1994) relates to the protective effect of glycoproteins of Newcastle disease virus expressed in insect cells following immunization with recombinant glycoproteins. Hulst et al., J. Virol. 67:5435–5442 (1993) pertains to the use of purified recombinant vaccine glycoprotein made in insect cells that protected swine from infection with the hog cholera virus.

There are vaccines where whole insect cells or insect cell membrane fractions containing a selected antigen are used. For example, McCown et al., Am. J. Trop. Med. Hyg. 42:491–499 (1990), use Spodoptera insect whole cells expressing Japanese Encephalitis Virus (JEV) glycoprotein E to immunize and protect mice against JEV. Putnak et al., Am. J. Trop. Med. Hyg. 45:159–167 (1991), use a microsomal membrane fraction of insect cells infected with a baculovirus expressing a Dengue-1 envelope glycoprotein to immunize and protect mice against challenge with Dengue-1 virus.

The insect cell line of the present invention is useful in the baculovirus expression system, also known in the art as "BEVS", or as an adjuvant, as disclosed in U.S. Ser. No. 08/965,698, filed Nov. 7, 1997.

In the baculovirus expression system, an inserted nucleic acid molecule, e.g., the foreign gene, the heterologous or exogenous nucleic acid molecule, for instance, DNA, is inserted into an insect virus vector, e.g., in a baculovirus vector, which is then used to infect cells of the invention cell line, for expression of the DNA. The DNA preferably encodes an expression product comprising at least one epitope of interest or antigen (including allergen).

Similarly, when the inventive insect cell line is used as an adjuvant, an immunological or vaccine composition of the invention (including the cell line as an adjuvant) can include at least one epitope of interest or an antigen.

With respect to these terms, reference is made to documents cited herein and the following discussion, and generally to Kendrew, *The Encyclopedia Of Molecular Biology*, Blackwell Science Ltd., 1995 and Sambrook, Fritsch and Maniatis, *Molecular Cloning, A Laboratory Manual*, 2nd Ed., Cold Spring Harbor Laboratory Press, 1982 ("Maniatis et al., 1982").

An epitope of interest is an immunologically relevant region of an antigen or immunogen or immunologically active fragment thereof, e.g., from a pathogen or toxin of veterinary or human interest.

An epitope of interest can be prepared from an antigen of a pathogen or toxin, or from another antigen or toxin which elicits a response with respect to the pathogen or toxin, e.g., from an antigen of a human or veterinary pathogen or toxin, or from another antigen or toxin which elicits a response with respect to such a human or veterinary pathogen or toxin, such as, for instance: a Morbillivirus antigen, e.g., a canine distemper virus or measles or rinderpest antigen such as HA or F; a rabies glycoprotein, e.g., rabies glycoprotein G; an avian influenza antigen, e.g., turkey influenza HA, Chicken/Pennsylvania/1/83 influenza antigen such as a nucleoprotein (NP) or influenza A/Jalisco/95 H5 Hemagglutinin; a human influenza antigen such as HA and/or NA; a bovine leukemia virus antigen, e.g., gp51, 30 envelope; a Newcastle Disease Virus (NDV) antigen, e.g., HN or F; a feline leukemia virus antigen (FeLV), e.g., FeLV envelope protein; a rous associated virus antigen such as RAV-1 env; matrix and/or preplomer of infectious bronchitis virus; a Herpesvirus glycoprotein, e.g., a glycoprotein, for instance from feline herpesvirus, equine herpesvirus, bovine herpesvirus, pseudorabies virus, canine herpesvirus, HSV, Marek's Disease Virus, herpesvirus of turkeys (HVT) or cytomegalovirus; a flavivirus antigen, e.g., a Japanese encephalitis virus (JEV) antigen, a Yellow Fever antigen, or a Dengue virus antigen; a malaria (Plasmodium) antigen, an immunodeficiency virus antigen, e.g., a feline immunodeficiency virus (FIV) antigen or a simian immunodeficiency virus (SIV) antigen or a human immunodeficiency virus antigen (HIV) such as gp120, gp160; a parvovirus antigen, e.g., canine parvovirus; an equine influenza antigen; a poxvirus antigen, e.g., an ectromelia antigen, a canary pox virus antigen or a fowl pox virus antigen; an infectious bursal disease virus antigen, e.g., VP2, VP3, VP4; a Hepatitis virus antigen, e.g., HBsAG; a Hantaan virus antigen; a *C. tetani* antigen; a mumps antigen; a pneumococcal antigen, e.g., PspA; a Borrelia antigen, e.g., OspA, OspB, OspC of Borrelia associated with Lyme disease such as *Borrelia burgdorferi*, *Borrelia afzelii* and *Borrelia garinii*; a chicken pox (varicella zoster) antigen.

Of course, the foregoing list is intended as exemplary, as the epitope of interest can be derived from any antigen of any veterinary or human pathogen or toxin; and, to obtain an epitope of interest, one can express an antigen of any veterinary or human pathogen or toxin.

In regard to the foregoing lists, with respect to Borrelia DNA, reference is made to: U.S. Pat. Nos. 5,777,095, 5,688,512, 5,582,990, and 5,523,089; Bergstrom et al., Mol. Microbiol., 3(4):479–486 (April 1989); Johnson et al., Infect. and Immun. 60:1845–1853 (1992); Johnson et al., Vaccine 13(12:1086–1094 (1995); and "The Sixth International Conference on Lyme Borreliosis: Progress on the Development of Lyme Disease Vaccine," Vaccine, 13(1) :133–135, 1995; and PCT publications WO 90/04411, WO 91/09870, WO 93/04175, and 96/06165.

With respect to pneumococcal epitopes of interest, reference is made to Briles et al. WO 92/14488 and U.S. Pat. Nos. 5,804,193, 5,753,463, 5,728,387, and 5,476,929.

With regard to influenza epitopes of interest and antigens, e.g., HA, NA, and recombinant baculovirus expression thereof, useful in the practice of the present invention, reference is made to Smith et al., U.S. application Ser. Nos. 08/120,601, filed Sep. 13, 1993, 08/453,848, filed May 30, 1995, now U.S. Pat. No. 5,858,368 and 08/430,971, filed Apr. 28, 1995 now U.S. Pat. No. 5,976,552, as well as to Johansson et al., "Supplementatior of conventional influenza A vaccine with purified viral reuraminidase results in a balanced and broadened immune response," Vaccine 16(9/10):1009–1015 (1998), Johansson et al., "Immunogenicity of influenza A virus N2 neuraminidase produced in insect larvae by baculovirus recombinants," Vaccine 9:841 (1995).

As to expression of adhesin and urease epitopes, chimeric proteins thereof, and chimeric nucleic acid molecules encoding such, reference is made to U.S. Ser. No. 09/111,169, filed Jul. 7, 1998. The insect cell line of the present invention is useful in the recombinant baculovirus expression of adhesin, urease, epitopes thereof, and chimeric proteins thereof.

With respect to DNA encoding epitopes of interest, which DNA can be expressed via a baculovirus expression system and using the cell line of the invention, attention is directed to documents cited herein, see, e.g., documents cited supra and documents cited infra, for instance: U.S. Pat. Nos. 5,174,993 and 5,505,941 (e.g., rabies glycoprotein (G), gene, turkey influenza hemagglutinin gene, gp51,30 envelope gene of bovine leukemia virus, Newcastle Disease Virus (NDV) antigen, FeLV envelope gene, RAV-1 env gene, NP (nucleoprotein gene of Chicken/Pennsylvania/1/83 influenza virus), matrix and preplomer gene of infectious bronchitis virus; HSV gD); U.S. Pat. No. 5,338,683 (e.g., DNA encoding Herpesvirus glycoproteins, inter alia); U.S. Pat. Nos. 5,494,807, 5,756,103, 5,762,938 and 5,766,599 (e.g., DNA encoding antigens from rabies, Hepatitis B, JEV, YF, Dengue, measles, pseudorabies, Epstein-Barr, HSV, HIV, SIV, EHV, BHV, HCMV, canine parvovirus, equine influenza, FeLV, FHV, Hantaan, C. tetani, avian influenza, mumps, NDV, inter alia); U.S. Pat. Nos. 5,503,834 and 5,759,841 (e.g., Morbillivirus, e.g., measles F, hemagglutinin, inter alia); U.S. Pat. No. 4,722,848 (e.g., HSV tk, HSV glycoproteins, e.g., gB, gD, influenza HA, Hepatitis B, e.g., HBsAg, inter alia); U.S. Pat. Nos. 5,514, 375, 5,744,140 and 5,744,141 (e.g., flavivirus structural proteins); U.S. Pat. No. 5,766,598 (e.g., Lentivirus antigens such as immunodeficiency virus antigens, inter alia); U.S. Pat. Nos. 5,658,572 and 5,641,490 (e.g., IBDV antigens, inter alia); WO 94/16716 (e.g., cytokine and/or tumor associated antigens, inter alia); U.S. Pat. Nos. 5,688,920, and 5,529,780 (e.g., canine herpesvirus antigens), PCT publication WO 96/3941 (e.g., cytomegalovirus antigens); and U.S. Pat. Nos. 5,756,101 and 5,766,597 (Plasmodium antigens).

As to antigens for use in vaccine or immunological, immunogenic or antigenic compositions (which antigens can be from BEVS using the inventive cell line or which compositions the cell line of the present invention can be an adjuvant), reference is made to the documents cited herein and the discussion set forth herein (see, e.g., documents cited supra) and also Stedman's Medical Dictionary (24th edition, 1982), e.g., definition of vaccine (for a list of antigens used in vaccine formulations; such antigens or epitopes of interest from those antigens can be used in the invention, as either an isolated product employed with an inventive adjuvant or an expression product of a recombinant insect virus or vector).

As to epitopes of interest, one skilled in the art can determine an epitope or immunodominant region of a peptide or polypeptide and ergo the coding DNA therefore from knowledge in the art, without undue experimentation, for instance, from the amino acid and corresponding DNA sequences of the peptide or polypeptide, as well as from the nature of particular amino acids (e.g., size, charge, etc.) and the codon dictionary, inter alia; and, in respect to this, attention directed to documents cited herein, including the aforementioned applications and patent. Accordingly, without any undue experimentation, the present invention can be used to practice recombinant baculovirus technology with the recombinant baculovirus containing DNA for any desired epitope of interest or antigen of any human or veterinary pathogen or toxin.

As a definitional matter, an immunological composition elicits an immunological response—local or systemic. The response can, but need not be protective. An immunogenic composition likewise elicits a local or systemic immunological response which can, but need not be, protective. An antigenic composition similarly elicits a local or systemic immunological response which can, but need not be, protective. A vaccine composition elicits a local or systemic protective response. Accordingly, the terms "immunological composition" and "immunogenic composition" and "antigenic composition" include a "vaccine composition" (as the three former terms can be protective compositions).

A better understanding of the present invention and of its many advantages will be had from the following non-limiting Examples, given by way of illustration.

EXAMPLES

Example 1

Sf900+
Establishment of a New Cell Line

A new cell line was established from Lepidoptera, Noctuidae, *Spodoptera frugiperda* (Sf900+) that was evolved from the *S. frugiperda* Sf-9 insect cell line through multiple rounds of limiting dilution and selection in a commercial serum-free insect medium supplemented with human insulin. Specifically, Sf-9 cells (ATCC CRL-1771) were propagated to passage 41 (4 passages at Texas A&M University, College Station, Tex.; 15 passages at the ATCC, Rockville, Md.; and an additional 22 passages at Protein Sciences Corporation, Meridan, Conn.) then stored in liquid nitrogen (Sf-9 Master Cell Bank No. 031793). A working bank of Sf-9 cells was produced and at passage 10, all of the serum-containing medium was removed by low speed centrifugation and the cells were suspended at a density of $0.5 \times 10^6$ cells/ml in commercial serum-free medium (Sf-900 SFM; Life Technologies, Grand Island, N.Y. 14072). This procedure was repeated every 5 days and on the third passage recombinant human insulin (Sigma I-2767) was added at a concentration of 0.2 μg/ml. The evolving cells were passaged an additional 34 times in 250 ml suspension cultures in Sf-900 SFM serum-free medium supplemented with 0.2 μg/ml human insulin. During the early passages cell death was 98% or more. This high level of cell mortality created the selective pressure needed for cells to undergo an evolutionary change.

It was surprisingly found that a new cell line, designated Sf900+ cells, had evolved with new and desirable properties. A Master Cell Bank was created with aliquots of Sf900+ cells in serum-free medium supplemented with 0.2 μg/ml insulin and 10% dimethyl sulfoxide (DMSO).

The surprising properties of the Sf900+ cell line include:
1) Sf900+ cells are genetically and morphologically distinct from the parent Sf9 cells,
2) Sf900+ cells replicate in serum-free medium,
3) Sf900+ cells grow as a suspension of single cells without significant clumping,
4) Sf900+ cells grow exponentially with a cell doubling time of 18–24 hours,
5) Sf900+ cells can be passed continuously for at least 6 months while maintaining a high level of viability (>98%),
6) Sf900+ cells are highly permissive to infection with A. californica NPV baculoviruses resulting in high titered virus stocks,
7) Sf900+ cells are useful for the production of recombinant DNA gene products following infection with baculovirus vectors,
8) Sf900+ cells are useful for the production and plaque-isolation of genetically engineered baculoviruses,
9) Sf900+ meet the general identity and safety requirements for cells set by government regulatory agencies, and
10) Sf900+ are suitable for the manufacture of biological pharmaceutical products following cGMP standards.

Deposited Material

Sf900+ insect cell line was deposited with the American Type Culture Collection (ATCC), 10801 University Boulevard, Manassas, Va. 20110-2009, under the terms of the Budapest Treaty, under ATCC Designation (Accession No.) CRL-12579 on Sep. 18, 1998 (ATCC CRL-12579).

Sf900+ Cell Line Safety

The safety of Sf900+ cell line was established following the recommendations of the Director, Center for Biological Evaluation and Research, Food and Drug Administration, Rockville, Md. (Points to Consider in the Characterization of Cell Lines Used to Produce Biologicals, issued May 17, 1993, U.S. Food and Drug Administration, Rockville, Md.). Safety tests were done including tests for sterility, tumorgenicity, and for contaminating mycoplasma, spiroplasma, and viruses. Studies to search for viruses in the Sf900+ cells included tests in insect and mammalian cell lines, embryonated eggs, and suckling mice; and to detect any contaminating retroviruses, assay for reverse transcriptase and electron microscopy. The Sf900+ cells are sterile, do not cause tumors to form in nude mice, and are free of any detectable adventitious agents including mycoplasma; spiroplasma; and viruses, including retroviruses.

Sf900+ Cell Line Identification

Light microscopy, karyology, and isoenzyme analysis were used to identify the new Sf900+ cell line. The cytoplasm of Sf900+ cells is lightly granulated and the nucleous usually contains several nucleoli. The Sf900+ cells are spherical with a mean diameter of 40 microns, approximately twice the diameter of Sf-9 cells. The wet biomass (weight of the cells following removal by centrifugation of the culture medium), when infected, is approximately 3-times greater than Sf-9 cells at a given cell density. The karyology of lepidopteran insect cells are well known to those skilled in the art as being polyploid with several hundred poorly defined chromosomes. Both the Sf-9 and Sf900+ cells have this characteristic chromosome pattern and can be distinguished from mammalian cells, such as Vero monkey kidney cells, which have a defined and limited number of chromosomes. Another method commonly used to identify cell lines is to compare the relative mobility of certain isoenzymes on protein gels. Approximately $10^7$ Sf900+, Sf9, and the mammalian Vero cells were prepared for isoenzyme analysis essentially as described by Corsaro and Fraser (*Characterization of clonal population of Heliothis zeal cell line IPLB-HA* 1075, In Vitro Cell. Div. Bio. 23(12):855–862, 1987). The isoenzyme patterns of Sf900+, Sf-9, and Vero cells were compared against the enzymes Lactate Dehydrogenase (LDH), Isocitrate Dehydrogenase (ICD), Phosphoglucose isomerase (PGI), and phosphoglucomutase (PGM) using the AuthentiKit System (Innovative Chemistry, Inc., Marshfield, Ma., 02050). The relative mobilities of the isoenzyme of the insect cells were distinctly different than that of the mammalian Vero cells (Table 1). Sf900+ cells have a similar but distinct isoenzyme pattern compared to the parent Sf-9 cells (Table 1), demonstrating that the Sf900+ cells are genetically different than the parent Sf-9 cells.

TABLE 1

| Cell line | Mobility of Isoenzymes (millimeters) | | | |
|---|---|---|---|---|
| | LDH | ICD | PGI | PGM |
| Sf-9 | 12.5 | nd* | 5.0 | 14.0 |
| Sf900+ | 11.0 | nd* | 5.0 | 14.0 |
| Vero | 8.0/2.0 | 8.0 | −2.0 | 6.0 |

*No enzyme detected.

Sf900+ Cell Growth Characteristic

The Sf900+ cells grow at 27° C.–28° C. in a commercial serum-free medium (Sf-900 SFM; Life Technologies, Grand Island, N.Y. 14072) supplemented with 0.2 μM recombinant human insulin. Routinely the cells are maintained in suspension cultures and are passed three times a week by dilution of the cells with fresh culture medium to $1.5 \times 10^6$ cell/ml. Following each dilution of the Sf900+ cells to $1.5 \times 10^6$ cell/ml their growth is exponential for 2–3 days. Sf900+ cells have a doubling time of 18–24 hours and reach a cell density in 3–4 days of $6–12 \times 10^6$ cells/ml with >95% of the cells remaining viable (FIG. 1).

Figure 2:
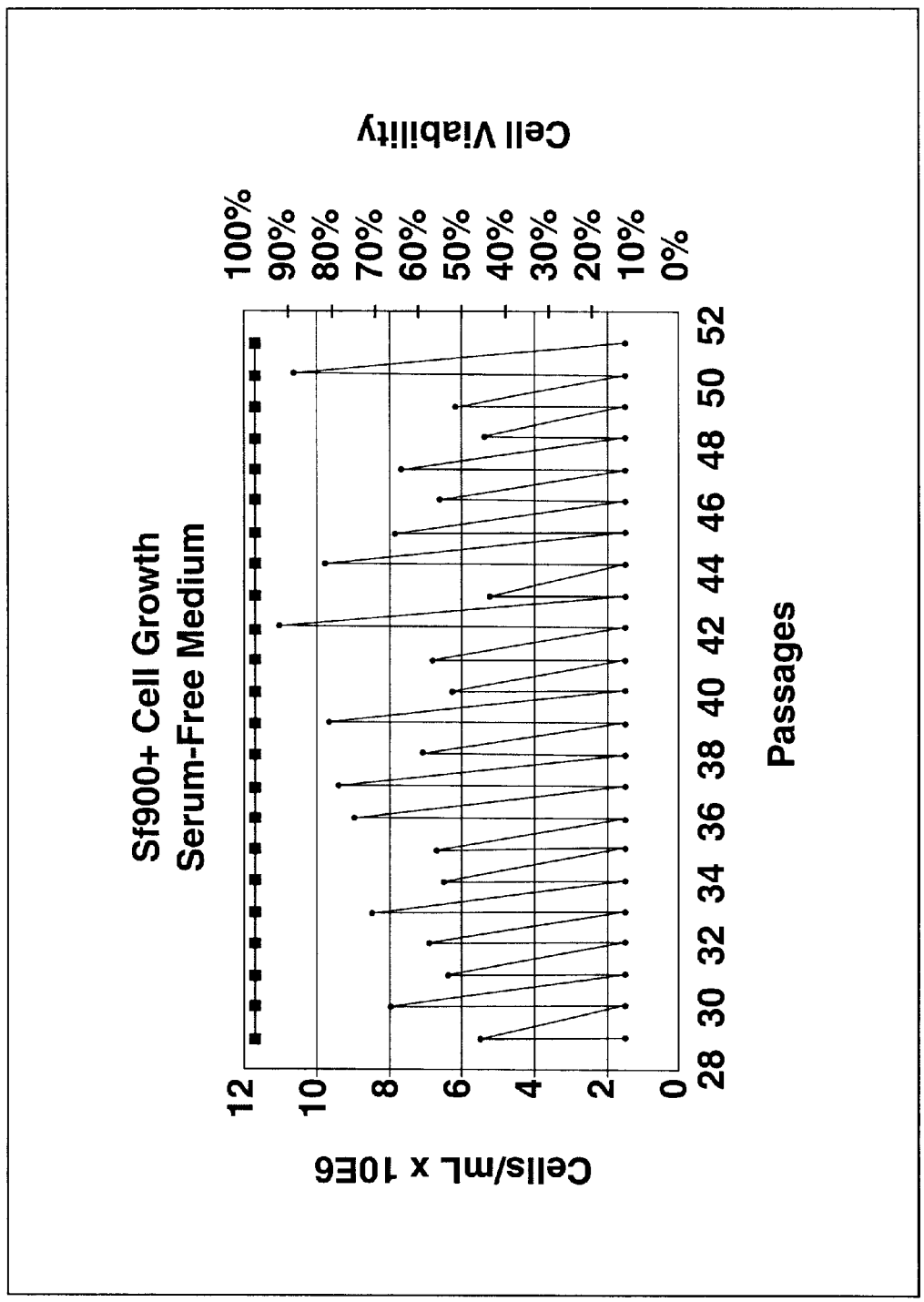
FIG. 2 shows that growth of Sf900+ cells over 50 passages in serum-free culture medium (Sf900+ cells were split to 1.5×10⁶ cells/ml every Monday, Wednesday, and Friday. At each passage the cells were counted and the viability measured. The graph shows the cell density at each day they were split (diamonds) and the cell viability (squares). The cells reached densities of 5–11×10⁶ cells/ml and remained about 98% viable); and, FIG. 3 shows that high titer of recombinant baculoviruses were produced from Sf900+ cells that were between passage 5 and 55 from the Sf900+ Master Cell Bank (Sf900+ cells were infected with recombinant AcNPV baculovirus at an MOI of 1.0 and the infected cells were harvested at 48–72 hours post infection. The infectious virus titers were measured in a standard plaque assay and found to be in the range of $0.6 \times 10^8$ to $2.2 \times 10^8$ pfu/ml).
Figure 3:
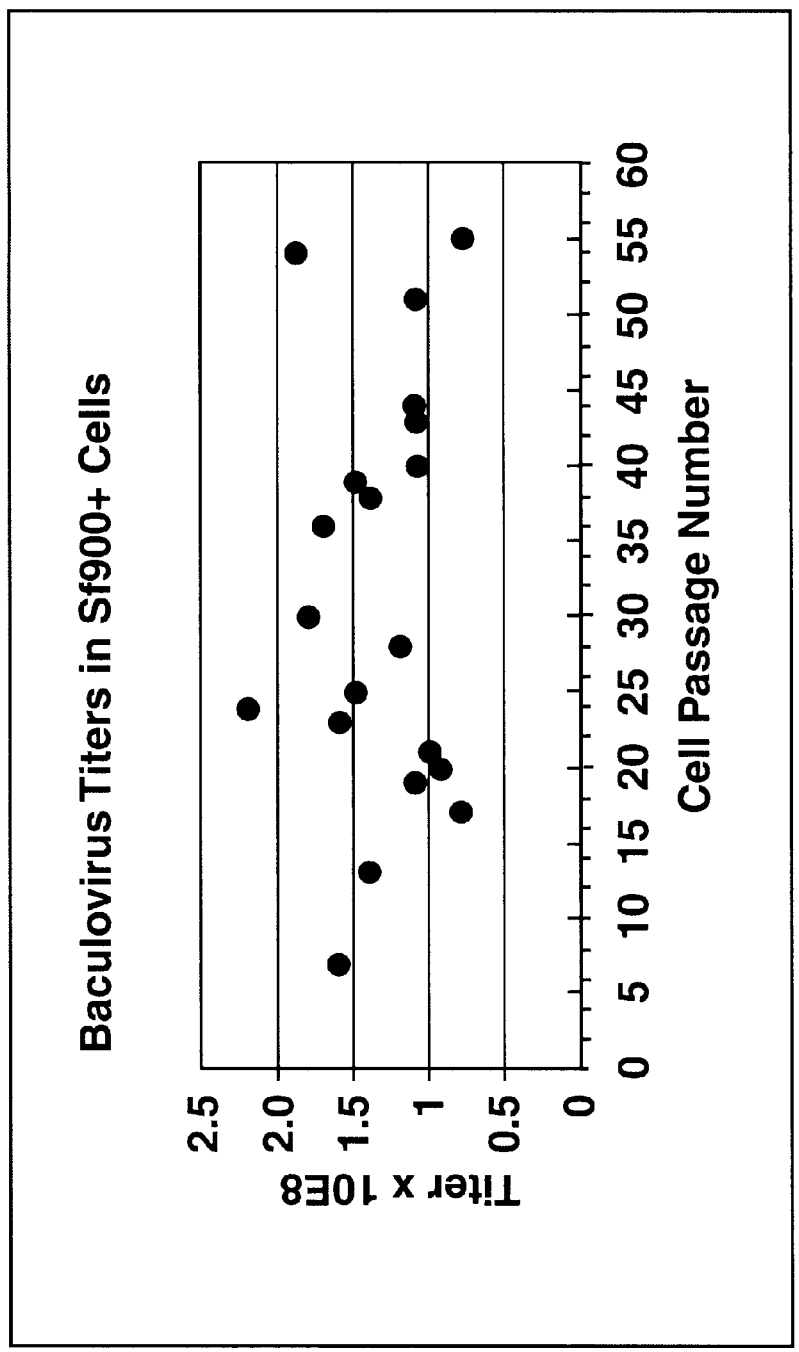

Routinely Sf900+ cells are passed with fresh medium three times a week (typically Monday, Wednesday, and Friday of each week). Under these conditions Sf900+ cells grow from $1.5 \times 10^6$ cell/ml to $5–11 \times 10^6$ cell/ml and are >95% viable (FIG. 2). It has surprisingly been found that the growth of Sf900+ cells can be maintained for 50 passages or longer without a significant change in growth characteristics (FIG. 3).

Biomass of Baculovirus Infected Sf900+ Cells in Large-Scale Bioreactors

The ideal insect cell line for the production of desired protein products would have a high biomass per unit volume of culture. If the proportion of the desired protein relative to the total cell biomass is constant, then the higher the cell biomass, the higher the yields of a desired product. The biomass of baculovirus-infected Sf900+ and Sf9 cells produced in 50 L biorectors were compared and the data is shown in Table 2.

When infected at a cell density of $1.5 \times 10^6$ cells/ml, the Sf900+ cells had the desired property of producing an average biomass of 14.8 g/l compared to only 5.4 g/l from the Sf9 cells or almost 3 times the biomass. The neuraminidase and HIV-1 gp160 gene products from the large-scale cultures were purified and used in several Phase I and Phase II human clinical trials approved by the U.S. FDA.

TABLE 2

Biomass of Sf900+ and Sf9 Cells Produced in 50L Bioreactors

| Run No. | Cell Type* | Cell Density | Volume (L) | Biomass (g) | Biomass (g/L) |
|---|---|---|---|---|---|
| 9723 | Sf900+ | 1.50E+06 | 45 | 525 | 11.7 |
| 9737 | Sf900+ | 1.50E+06 | 40 | 697 | 17.4 |
| 9741 | Sf900+ | 1.50E+06 | 45 | 795 | 17.7 |
| 9744 | Sf900+ | 1.50E+06 | 45 | 567 | 12.6 |
| Mean | | 1.50E+06 | 43.8 | 646 | 14.8 |
| 9505 | Sf9 | 1.45E+06 | 46 | 238 | 5.2 |
| 9601-F601 | Sf9 | 1.34E+06 | 45 | 239 | 5.3 |
| 9601-F602 | Sf9 | 1.41E+06 | 46 | 246 | 5.3 |
| 9601-F603 | Sf9 | 1.50E+06 | 46 | 259 | 5.6 |
| Mean | | 1.43E+06 | 45.8 | 246 | 5.4 |

*Sf900+ cells were infected with a recombinant baculovirus engineered to express influenza neuraminidase (strain A/Johannesburg/33/94 and Sf9 cells were infected with a recombinant baculovirus engineered to express HIV-1 gp160. Both cultures were infected at a MOI of 1 pfu/cell. There was no significant growth of the Sf900+ cells or the Sf9 cells following infection. Infected cells were harvested at about 72 hours post infection and separated from the culture medium by centrifugation. The supernatant was discarded and the weight of the wet cells was measured.

Lack of Cell Aggregation with Sf900+ Cells

The degree of aggregation of Sf900+ cells was measured at a low ($1.38 \times 10^6$ cells/ml) and high ($6.56 \times 10^6$ cells/ml) cell density. Sf900+ cells were counted using standard procedures in a hemocytometer. The number of aggregates with 5 or more cells in a clump and the number of viable and dead cells were recorded. The cell viability was >99% in both the low and high-density cultures. Only 1.4% and 1.3% of the cells were aggregated in the low and high density cultures respectively, demonstrating the surprising result that Sf900+ cells grow in serum-free medium essentially as a single-cell suspension of cells. The fact that Sf900+ cells do not aggregate avoids the problem associated with adding reagents or chemicals to the culture to prevent aggregation. Any aggregation would severely reduce the productivity of the cells due to diffusional barriers for nutrients or by-products or due to reducing their accessibility to virus infection.

TABLE 3

Aggregation of Sf900+ Cells at Low and High Cell Densities

| | Low Density | | High Density | |
|---|---|---|---|---|
| | Counts | Clumps | Counts* | Clumps |
| | 130 | 1 | 149 | 1 |
| | 105 | 1 | 122 | 2 |
| | 157 | 4 | 124 | 1 |
| | 160 | 2 | 130 | 3 |
| Mean | 138 | 2 | 131 | 2 |
| cells/ml | $1.38 \times 10^6$ | | $6.56 \times 10^6$ | |
| % Clumps | | 1.4 | | 1.3 |

*(The high-density culture was diluted 1/5 with culture medium before counting.)

Replications of Baculoviruses in Sf900+ Cells

A noteworthy characteristics of the Sf900+ cells is that they produce very high titers of A. californica NPV baculovirus. For example, Sf900+ cells were seeded at $1.5 \times 10^6$ cells/ml and can be used for 50 passages or longer for baculovirus production. FIG. 3 shows examples of the titers as measured in a standard plaque assay of baculoviruses observed in Sf900+ cells from passage 5 to passage 55. Sf900+ cells were obtained from the Master Cell Bank and passed three times weekly for up to 55 passages. Cells from passages 5 to 55 were diluted to $1.5 \times 10^6$ cells/ml and infected with recombinant AcNPV baculoviruses at a multiplicity of infection (MOI) of 1.0. At 48–72 hours post infection, the cells were harvested and the cells removed by low speed configuration. The titers of recombinant baculovirus were measured in a standard plaque assay. Very high virus titers of A. californica NPV of $0.6 \times 10^8$ to $2.2 \times 10^8$ plaque forming units (pfu) per milliliter of culture were generated in cells up to passage 55.

Production of Gene Products in Sf900+ Cells

The ideal insect cell line could be used to produce recombinant proteins from any genetic source and, ideally, high levels of the desired protein product would be produced in a biologically active form. To demonstrate that Sf900+ cells can produce wide range of foreign gene products, Sf900+ cells were infected at a density of $1.5-3.0 \times 10^6$ cells/ml at an MOI of 1.0 with various AcNPV expression vectors containing the genes listed in Table 3. The organism of origin for the foreign gene and specific genes were cloned into AcNPV expression vectors according to standard methods. The relative yields, protein modification, location in the cells, and physical and biological properties of the recombinant proteins are given. The yields of recombinant proteins were quantified using standard chemical and immunological methods and scored as low (<1 mg/l), moderate (1–10 mg/l), or high (10–1000 mg/l).

Specific Methods for Producing Gene Products in Sf900+ Cells: Influenza Virus Hemagglutinins from H1, H2, H5, H7, and B strains Reference is made to U.S. Pat. No. 5,762,939 and to allowed U.S. application Ser. No. 08/453,848, incorporated herein by reference, for a detailed description of the cloning, baculovirus expression, fermentation and purification procedures, for the production of influenza virus hemagglutinins. Thus, hemagglutinin is obtained with at least 95% purity.

Influenza Virus Neuraminidase

The sequence of the Influenza Virus Neuraminidase (NA) (strain A/Johannesburg/33/94) is available from GenBank (accession no. U43425). The NA gene was amplified by PCR from viral cDNA using primers designed against a consensus sequence (made by aligning NA gene from GenBank) A 5' PCR primers was made that began at the ATG start codon of the full-length protein. A 3' primer was designed to terminate after the natural stop codon of the NA open reading frame. After PCR amplification, the resulting NA gene fragment was inserted into the pMGS3 baculovirus transfer plasmid using standard procedures (Sambrook, J, Fritsch, E. F., and Maniatis, T. 1989. Molecular cloning: a laboratory manual. 2nd ed. Cold Spring Harbor Laboratory Press, Cold Spring Harbor, N.Y.). The resulting transfer plasmid contained the coding region from NA downstream of the polyhedrin promoter, flanked by AcNPV DNA from the EcoRI "I" fragment (Summers and Smith 1987, supra). Confirmation of the correct NA coding sequence was determined by DNA sequence analysis.

Genomic baculovirus DNA and the transfer plasmid containing the NA gene were mixed, co-precipitated with calcium chloride, and Sf900+ cells were transfected as described (Summers and Smith 1987, supra). Recombinant viruses were identified by plaque morphology and several were further plaque purified. Recombinant viruses capable of expressing NA in infected Sf900+ cells were identified and used as baculovirus expression vectors to produce recombinant NA in Sf900+ cells.

Sf900+ cells, at a cell density of $1.5 \times 10^6$ cells/ml are infected with the baculovirus expression vector containing the NA gene at an MOI of 1.0. Sf900+ cells are harvested by centrifugation 72 hours post infection. The cell pellet containing RNA is stored at −70° C. for further processing.

Product purification follows centrifugation, filtration and chromatographic procedures analogous to those presented for influenza virus hemagglutinin. Thus, NA can be obtained with at least 95% purity.

Human Immuno-deficiency Virus, Type 1 (HIV-1) HIV-1 env gp120

The sequence of the HIV-1 env gp120 (gp120) is available from GenBank (accession no. M19921). The plasmid pNL4-3 (Adachi et al. J. Virol. 59: 284–291 (1986)) was graciously obtained from Dr. Malcolm Martin's laboratory. A construct was made in which gp120's natural signal peptide was replaced by a baculovirus signal peptide. A 5' PCR primer was made that began at the N-terminal residue of the mature peptide. A 3' primer was designed to place a stop codon at the end of the gp120 portion of the env open reading frame. After PCR amplification, the resulting gp120 gene fragment was inserted into the pMGS12 baculovirus transfer plasmid using standard procedures (Sambrook, J, Fritsch, E. F., and Maniatis, T. 1989. Molecular cloning: a laboratory manual. 2nd ed. Cold Spring Harbor Laboratory Press, Cold Spring Harbor, N.Y.). The resulting transfer plasmid contained the coding region from gp120 downstream of the polyhedrin promoter, flanked by AcNPV DNA from the EcoRI "I" fragment (Summers and Smith 1987, supra). Confirmation of the correct gp120 coding sequence was determined by DNA sequence analysis.

Genomic baculovirus DNA and the transfer plasmids containing the gp120 gene were mixed, co-precipitated with calcium chloride, and Sf900+ cells were transfected as described (Summers and Smith 1987, supra). Recombinant viruses were identified by plaque morphology and several were further plaque purified. Recombinant viruses capable of expressing gp120 in infected Sf900+ cells were identified and used as baculovirus expression vectors to produce recombinant gp120 in Sf900+ cells.

Sf900+ cells, at a cell density of $1.5 \times 10^6$ cells/ml are infected with the baculovirus expression vector containing the gp120 gent at an MOI of 1.0. Sf900+ cells are harvested by centrifugation 72 hours post infection. The cell pellet is discarded and the supernatant containing secreted recombinant gp120 is stored at 4° C. for further processing.

Product purification follows centrifugation, filtration and chromatographic procedures analogous to those presented for influenza virus hemagglutinin. Thus, HIV-1 env gp 120 can be obtained with at least 95% purity.

Human Immuno-deficiency Virus, Type 1 (HIV-1) HIV gag p55

The sequence of the human (HIV-1) HIV gag (p55) is available from GenBank (accession no. M15654). The p55 gene obtained as a plasmid containing the BH10 clone of LAV/HTLV-IIIB strain of HIV-1 (Hahn et al. Nature 312: 166–69 (1984)) was used as the template to amplify p55 coding sequences by PCR. A 5' PCR primer was made that began at the ATG start codon of the full-length protein. A 3' primer was designed to terminate after the natural stop codon of the p55 open reading frame. After PCR amplification, the resulting p55 gene fragment was inserted into pMGS3 baculovirus transfer plasmid using standard procedures (Sambrook, J, Fritsch, E. F., and Maniatis, T. 1989. Molecular cloning: a laboratory manual. 2nd ed. Cold Spring Harbor Laboratory Press, Cold Spring Harbor, N.Y.). The resulting transfer plasmid contained the coding region from p55 downstream of the polyhedrin promoter, flanked by AcNPV DNA from the EcoRI "I" fragment (Summers and Smith 1987, supra). Confirmation of the correct p55 coding sequence was determined by DNA sequence analysis and compared to Ratner et al. Nature 313: 277–284 (1985).

Genomic baculovirus DNA and the transfer plasmids containing the p55 gene were mixed, co-precipitated with calcium chloride, and Sf900+ cells was transfected as described (Summers and Smith 1987, supra). Recombinant viruses were identified by plaque morphology and several were further plaque purified. Recombinant viruses capable of expressing p55 in infected Sf900+ cells were identified and used as baculovirus expression vectors to produce recombinant p55 in Sf900+ cells.

Sf900+ cells, at a cell density of $1.5 \times 10^6$ cells/ml are infected with the baculovirus expression vector containing the p55 gene at an MOI of 1.0. Sf900+ cells are harvested by centrifugation 72 hours post infection. The cell pellet is discarded and the supernatant containing secreted recombinant p55 is stored at 4° C. for further processing.

Product purification follows centrifugation, filtration and chromatographic procedures analogous to those presented for influenza virus hemagglutinin. Thus, HIV gag p55 can be obtained with at least 95% purity.

CD4

The sequence of the human CD4 (CD4) is available from GenBank (accession no. M12807). The CD4 gene isolated from H9 human T-cell line (ATCC HTB 176) cDNA was used as a template to amplify CD4 coding sequences by PCR. A construct was made in which CD4's natural signal peptide was replaced by a baculovirus signal peptide and the natural transmembrane domain was removed. A 5' PCR primer was made that began at the N-terminal residue of the mature peptide. A 3' primer was designed to terminate before the natural transmembrane domain and insert a stop codon. After PCR amplification, the resulting CD4 gene fragment was inserted into the pMGS12 baculovirus transfer plasmid using standard procedures (Sambrook, J, Fritsch, E. F., and Maniatis, T. 1989. Molecular cloning: a laboratory manual. 2nd ed. Cold Spring Harbor Laboratory Press, Cold Spring Harbor, N.Y.). The resulting transfer plasmid contained the coding region from CD4 downstream of the polyhedrin promoter, flanked by AcNPV DNA from the EcoRI "I" fragment (Summers and Smith 1987, supra). Confirmation of the correct CD4 coding sequence was determined by DNA sequence analysis and compared to a published sequence (Maddon et al. Cell 42: 93–104 (1985)).

Genomic baculovirus DNA and the transfer plasmids containing the CD4 gene were mixed, co-precipitated with calcium chloride, and Sf900+ cells were transfected as described (Summers and Smith 1987, supra). Recombinant viruses were identified by plaque morphology and several were further plaque purified. Recombinant viruses capable of expressing CD4 in infected Sf900+ cells were identified and used as baculovirus expression vectors to produce recombinant CD4 in Sf900+ cells.

Sf900+ cells, at a cell density of $1.5 \times 10^6$ cells/ml are infected with the baculovirus expression vector containing the CD4 gene at an MOI of 1.0. Sf900+ cells are harvested by centrifugation 72 hours post infection. The cell pellet is discarded and the supernatant containing secreted recombinant CD4 is stored at 4° C. for further processing.

Product purificagtion follows centrifugation, filtration and chromatographic procedures analogous to those presented for influenza virus hemagglutinin. Thus, CD4 can be obtained with at least 95% purity.

Human Erythropoietin

The sequence of human erythropoietin (EPO) is available from GenBank (accession no. X02157). The human EPO gene isolated from a genomic library in bacteriophage Lambda EMBL-3 was used as template to amplify EPO coding sequences by PCR. A construct was made in which EPO's natural signal peptide was replaced by a baculovirus signal peptide. A 5' PCR primer was made that began at the N-terminal residue of the mature peptide. A 3' primer was designed to terminate after the natural stop codon of the EPO open reading frame. After PCR amplification, the resulting EPO gene fragment was inserted into the pMGS12 baculovirus transfer plasmid using standard procedures (Sambrook, J, Fritsch, E. F., and Maniatis, T. 1989. Molecular cloning: a laboratory manual. 2nd ed. Cold Spring Harbor Laboratory Press, Cold Spring Harbor, N.Y.). The resulting transfer plasmid contained the coding region from EPO downstream of the polyhedrin promoter, flanked by AcNPV DNA from the EcoRI "I" fragment (Summers and Smith 1987, supra). Confirmation of the correct EPO coding sequence (Jacobs et al. Nature 313 806–10 (1985)) was determined by DNA sequence analysis.

Genomic baculovirus DNA and the transfer plasmids containing the EPO gene were mixed, co-precipitated with calcium chloride, and Sf900+ cells were transfected as described (Summers and Smith 1987, supra). Recombinant viruses were identified by plaque morphology and several were further plaque purified. Recombinant viruses capable of expressing EPO in infected Sf900+ cells were identified and used as baculovirus expression vectors to produce recombinant EPO in Sf900+ cells.

Sf900+ cells, at a cell density of $1.5 \times 10^6$ cells/ml are infected with the baculovirus expression vector containing the EPO gene at an MOI of 1.0. Sf900+ cells are harvested by centrifugation 72 hours post infection. The cell pellet is discarded and the supernatant containing secreted recombinant EPO ("rEPO") is stored at 4° C. for further processing.

Product purification follows centrifugation, filtration and chromatographic procedures analogous to those presented for influenza virus hemagglutinin. Thus, EPO can be obtained which is purified to substantial homogeneity or to at least 95% purity. With respect to EPO, DNA encoding EPO and substantial homogeneity of EPO, reference is also made to Lin, U.S. Pat. Nos. 4,703,008, 5,441,868, 5,574, 933, 5,618,698, 5,621,080, and 5,756,349. In addition, reference is also made to Wojchowski et al., "Active Human Erythropoietin Expressed in Insect Cells, Using a Baculovirus Vector: A Role For N-Linked Oligosaccharide", Biochimica et Biophysica Acta 910:224–32 (1987), Quelle et al., "High-Level Expression and Purification of a Recombinant Human Erythropoietin Produced Using a Baculovirus Vector", Blood, 74(2):652–57 (1989), Quelle et al., "Phosphorylatable and Epitope-Tagged Human Erythropoietins: Utility and Purification of Native Baculovirus-Derived Forms", Protein Expression and Purification 3:461–69 (1992), and U.S. Pat. Nos. 5,322,837 and 4,677,195. In contrast to any prior EPO from baculovirus expression, EPO in accordance with the present invention can be purified to at least 95% purity or to substantial homogeneity; and, as indicated in Table 3 the EPO in accordance with the present invention stimulates erythropoiesis.

As a particular purification procedure, centrifuged culture supernatant containing rEPO is pH adjusted to pH 8.0 with Tris-base. Proteinatious and non-proteinatious materials bind to precipitating salts, mainly calcium hydroxide, and are removed by centrifugation while rEPO remains in the supernatant. The resulting rEPO containing supernatant is diafiltered into 10 mM Tris-Cl buffer pH 8.0.

The diafiltered rEPO containing supernatant is applied onto DEAE Sepharose and equilibrated with 10 mM Tris-Cl buffer pH 8.0. The rEPO binds weakly and is recovered in the flow-through while contaminants remain bound to the column. Diafiltration into low-conductivity buffer prior to anion-exchange chromatography ensures stronger binding of contaminants and higher degree of purification at this step. The collected DEAE flow-through is diafiltered into 10 mM sodium malonate buffer pH 6.0 and applied to CM Sepharose equilibrated with the 10 mM sodium malonate pH 6.0 buffer. The rEPO binds to CM Sepharose while contaminants flow through the column. The column is then washed with 10 mM sodium malonate buffer pH 6.0 containing 100 mM NaCl, to further remove contaminants. The elute rEPO from the column, a 10 mM sodium malonate buffer pH 6.0 containing 150 mM NaCl is used.

The eluant containing rEPO is applied to a second CM Sepharose column equilibrated with 10 mM sodium malonate buffer pH 6.0. It is then washed with 10 mM sodium phosphate buffer pH 7.0 and finally, rEPO is eluted in PBS (10 mM sodium phosphate, 150 mM NaCl).

The EPO expressed is glycosylated and has a molecular weight of approximately 25 kD. The amino acid sequence is the same as or analogous to that set forth in literature and patents cited herein. It is quite surprising that the EPO in accordance with the present invention stimulates erythropoiesis as the inventive EPO has glycosylation which does not include sialic acid residues, and there is no O-glycosylation because the EPO is from baculovirus expression; and, any reported recombinant EPO from baculovirus expression heretofore was reported as having no such activity.

In particular, urinary EPO (also known as uEPO) and recombinant EPO produced in mammalian cells are heterogenously glycosylated with complex N- and O-linked oligosaccharides, including sialic acid N-terminal residues, and are acidic proteins, whereas EPO from recombinant baculovirus expression can have a comparably simple saccharide constitution and relative homogeneity, with no sialic acid residues, neutral high-mannose moieties predominating and the highly basic charge density of EPO retained, because of the limited capacity of insect cells to process N-linked oligosaccharides.

Certain literature such as Quelle et al., Blood, supra, at 656, indicates that EPO from expression by insect cells infected with recombinant baculovirus containing DNA coding for EPO is not biologically active due to the lack of sialic acid residues. Further, there is a body of literature asserting that EPO's "heavy glycosylation" and sialic acid residues are essential for biological activity, see, e.g., Marmont, Tumori 83(4 Suppl 2):S3-15 (1997), Morimoto et al., Glycoconj J 13(6):1013–20 (1996), Higuchi et al., J. Biol. Chem. 267(11):7704–9 (Apr. 15, 1992), Takeuchi et al., Glycobiology 1(4):337–46 (1991), Tsuda et al., Eur. J. Biochem. 188(2):405–11 (1990), Takeuchi et al. J. Biol. Chem. 265(21):12127–30 (1990), Fakuda et al., Blood 73(1):84–9 (1989); Matsumoto et al. Plant Mol. Bio. 27(6):1163–72 (1995) (EPO from tobacco cells lacking sialic acid residues lacked activity).

In contrast, the recombinant EPO of the present invention has an activity of at least 200,000 U/mg (indeed about 500,000 U/mg) and stimulates erythropoiesis. In further contrast to prior EPO, the EPO of the present invention can be isolated using anion exchange and cation exchange chromatography, as opposed to reverse chromatography (used for isolating prior EPO).

Thus, the recombinant EPO of the present invention is distinct from and surprisingly superior to prior EPO.

Thrombospondin

The sequence of the human thrombospondin (TSP) is available from GenBank (accession no. X14787). The human TSP gene graciously obtained as a plasmid containing full-length TSP cDNA from Dr. Noel Bauck's laboratory was used as the template to amplify TSP coding sequences by PCR. A construct was made in which TSP's natural signal peptide was replaced by a baculovirus signal peptide. A 5' PCR primer was made that began at the N-terminal residue of the mature peptide. A 3' primer was designed to terminate after the natural stop codon of the TSP open reading frame. After PCR amplification, the resulting TSP gene fragment was inserted into the pMGS12 baculovirus transfer plasmid using standard procedures (Sambrook, J, Fritsch, E. F., and Maniatis, T. 1989. Molecular cloning: a laboratory manual. 2nd ed. Cold Spring Harbor Laboratory Press, Cold Spring Harbor, N.Y.). The resulting transfer plasmid contained the coding region from TSP downstream of the polyhedrin promoter, flanked by AcNPV DNA from the EcoRI "I" fragment (Summers and Smith 1987, supra). Confirmation of the correct TSP coding sequence was determined by DNA sequence analysis and compared with Hennessy et al. J. Cell Biol. 108:729–736 (1989).

Genomic baculovirus DNA and the transfer plasmids containing the TSP gene were mixed, co-precipitated with calcium chloride, and Sf900+ cells were transfected as described (Summers and Smith 1987, supra). Recombinant viruses were identified by plaque morphology and several were further plaque purified. Recombinant viruses capable of expressing TSP in infected Sf900+ cells were identified and used as baculovirus expression vectors to produce recombinant TSP in Sf900+ cells.

Sf900– cells, at a cell density of $1.5 \times 10^6$ cells/ml are infected with the baculovirus expression vector containing the TSP gene at an MOI of 1.0 Sf900+ cells are harvested by centrifugation 72 hours post infection. The cell pellet containing recombinant TSP is stored at $-70°$ C. for further processing.

Product purification follows centrifugation, filtration and chromatographic procedures analogous to those presented for influenza virus hemagglutinin. Thus, TSP having at least 95% purity can be obtained.

Carcinoembryonic antigen (CEA)

The sequence of the human Carcinoembryonic antigen (CEA) is available from GenBank (accession no. M15042). The Human CEA isolated from LS174T human colon adenocarcinoma cell line cDNA (ATCC CL188) was used as template to amplify CEA coding sequences by PCR. A construct was made in which CEA's natural signal peptide was replaced by a baculovirus signal peptide and the natural transmembrane domain was removed. A 5' PCR primer was made that began at the N-terminal residue of the mature peptide. A 3' primer was designed to terminate before the natural transmembrane domain and insert a stop codon. After PCR amplification, the resulting CEA gene fragment was inserted into the pMGS12 baculovirus transfer plasmid using standard procedure (Sambrook, J, Fritsch, E. F., and Maniatis, T. 1989. Molecular cloning: a laboratory manual. 2nd ed. Cold Spring Harbor Laboratory Press, Cold Spring Harbor, N.Y.). The resulting transfer plasmid contained the coding region from CEA downstream of the polyhedrin promoter, flanked by AcNPV DNA from the EcoRI "I" fragment (Summers and Smith 1987, supra). Confirmation of the correct DEA coding sequence was determined by DNA sequence analysis.

Genomic baculovirus DNA and the transfer plasmids containing the CEA gene were mixed, co-precipitated with calcium chloride, and Sf900+ cells are transfected as described (Summers and Smith 1987, supra). Recombinant viruses were identified by plaque morphology and several were further plaque purified. Recombinant viruses capable of expressing CEA in infected Sf900+ cells were identified and used as baculovirus expression vectors to produce recombinant CEA in Sf900+ cells.

Sf900+ cells, at a cell density of $1.5 \times 10^6$ cells/ml are infected with the baculovirus expression vector containing the CEA gene at an MOI of 1.0. Sf900+ cells are harvested by centrifugation 72 hours post infection. The cell pellet is discarded and the supernatant containing secreted recombinant CEA is stored at $4°$ C. for further processing.

Product purification follows centrifugation, filtration chromatographic procedures analogous to those presented for influenza virus hemagglutinin. Thus, CEA having a purity of at least 95% can be obtained.

TABLE 4

| Organism | Gene in AcNPV Vectors | Production of Gene Product | Modification; Location in Sf900+ Cells | Physical and Biological Properties |
|---|---|---|---|---|
| Influenza Virus | Hemagglutinins from H1, H2, H5, H7, and B strains | Moderate to High | Glycosylated; cytoplasmic membranes | 66–70 Kd, trimers; agglutinates red blood cells |
| | Neuraminidase | Moderate | Glycosylated; cytoplasmic membranes | 60 Kd, tetramers; with sialidase activity |
| Human Immunodeficiency Virus, Type 1 (HIV-1) | HIV-1 env gp120 | High | Glycosylated; secreted | 110 kD, binds with high affinity to human CD4 receptor |
| | HIV gag p55 | High | Myristylated; secreted | 55 kD, forms virus-like particles |
| Human | CD4 | High | Glycosylated; secreted | 50 kD, binds with high affinity to HIV-1 gp120 |
| | Erythropoietin | High | Glycosylated; secreted | 25 kD, monomers; stimulates erythropoiesis |
| | Thrombospondin | High | Glycosylated; cytoplasmic membranes | 180 kD, Anti-angiogenic |
| | Carcinoembryonic antigen (CEA) | High | Glycosylated; secreted | 120 kD, induces anti-CEA immune responses in humans |

EXAMPLE 2

Adjuvant Uses

Sf900– cells are used in accordance with U.S. Ser. No. 08/965,698, filed Nov. 7, 1997 as an adjuvant in immunological, immune or vaccine compositions. Advantages of Example 1 are observed.

EXAMPLE 3

Expression Uses

The BEVS is used with other exogenous DNA encoding an antigen or an epitope of interest from an antigen, such as an antigen aforementioned, e.g., adhesin and/or urease or epitope(s) thereof such as a chimeric protein of adhesin and urease or of an epitope of interest of each of adhesin and urease. The insect cell line used with the BEVS is the inventive Sf900+ cell line. The antigen or epitope of interest is expressed, and the advantages of Example 1 are observed.

The antigen or epitope is optionally thereafter formulated into a vaccine, immune or immunological composition for administration orally or intragastrically, or for parenteral (i.e., intramuscular, intradermal or subcutaneous) administration of for other orifice administration, e.g., perlingual (i.e., oral), intragastric, mucosal including intraoral, intraanal, intravaginal, and the like administration.

Having thus described in detail preferred embodiments of the present invention, it is to be understood that the invention defined by the appended claims is not to be limited to particular details set forth in the above description as many apparent variations thereof are possible without departing from the spirit or scope of the present invention.

What is claimed is:

1. An insect cell line designated ATCC CRL-12579 or an insect cell line having all of the identifying characteristics of ATCC CRL-12579.

2. An insect cell line established from Lepidoptera, Noctuidae, *Spodoptera frugiperda* Sf-9 designated ATCC CRL-1771, through dilution and selection in a serum-free insect medium supplemented with added human insulin, which grows in a serum-free insect medium supplemented with added human insulin, and which is genetically and morphologically distinct from the parent Sf9 cells.

3. The insect cell line of claim 2 obtained from
   passaging Sf-9 cells for 41 passages to obtain a first working bank of cells;
   passaging the first working bank of cells for an additional 10 passages and at passage 10 removing serum-containing medium to obtain a second working bank of cell;
   suspending the second working bank of cells in serum-free medium until a third passage wherein insulin is added to the medium to obtain insulin-contacted cells; and,
   passaging the insulin-contacted cells in insulin-containing serum-free medium for a further 34 passages.

4. The insect cell line of claim 2 having one or both of the following characteristics:
   cells which grow as essentially a suspension of single cells, and
   cells which can be passed continuously for at least 6 months while maintaining a level of viability of >98%.

5. An insect cell line established from Lepidoptera, Noctuidae, *Spodoptera frugiperda* Sf-9, designated ATCC CRL-1771, through dilution and selection in a serum-free insect medium supplemented with added human insulin, which grows in a serum-free insect medium supplemented with added human insulin, and which is genetically and morphologically distinct from the parent Sf9 cells, and, which grow as essentially a suspension of single cells, and which can be passed continuously for at least 6 months while maintaining a level of viability of >98%.

6. A method for obtaining an insect cell line comprising subjecting Lepidoptera, Noctuidae, *Spodoptera frugiperda* Sf9 cells designated ATCC CRL-1771 to dilution and selection in a serum-free insect medium supplemented with added human insulin.

7. The method of claim 6 comprising:
   passaging Sf-9 cells for 41 passages to obtain a first working bank of cells;
   passaging the first working bank of cells for an additional 10 passages and at passage 10 removing serum-containing medium to obtain a second working bank of cells;
   suspending the second working bank of cells in serum-free medium until a third passage wherein insulin is added to the medium to obtain insulin-contacted cells; and,
   passaging the insulin-contacted cells in insulin-containing serum-free medium for a further 34 passages.

8. A method for expressing oxygenous coding DNA from a baculovirus expression system comprising a recombinant baculovirus that comprises the exogenous coding DNA comprising injecting insect cells from an insect cell line as claimed in any one of claims 1, 2, 3, 4 or 5, with the recombinant baculovirus.

9. The method of claim 8 wherein the exogenous coding DNA encodes erythropoietin.

10. The method of claim 9 wherein the erythropoietin has an activity of about 500,000 U/mg.

11. The method of claim 9 wherein the erythropoietin has an activity of about at least about 200,000 U/mg.

12. The method of claim 8 wherein the exogenous coding DNA encodes neuraminidase.

13. The method of claim 8 wherein the exogenous coding DNA encodes CD4.

14. The method of claim 8 wherein the exogenous coding DNA encodes thrombospondin.

15. The method of claim 8 wherein the exogenous coding DNA encodes CEA.

16. The method of claim 8 wherein the exogenous coding DNA encodes influenza hemagglutinin.

* * * * *

UNITED STATES PATENT AND TRADEMARK OFFICE
CERTIFICATE OF CORRECTION

PATENT NO. : 6,103,526

DATED : August 15, 2000

INVENTOR(S) : Smith, et al.

It is certified that error appears in the above-identified patent and that said Letters Patent is hereby corrected as shown below:

Claim 8, line 4, please change "injecting" to --infecting--.

Signed and Sealed this

Twenty-ninth Day of May, 2001

*Attest:*

NICHOLAS P. GODICI

*Attesting Officer*   *Acting Director of the United States Patent and Trademark Office*

UNITED STATES PATENT AND TRADEMARK OFFICE
CERTIFICATE OF CORRECTION

PATENT NO. : 6,103,526
DATED : August 15, 2000
INVENTOR(S) : Smith et al.

It is certified that error appears in the above-identified patent and that said Letters Patent is hereby corrected as shown below:

<u>Title page,</u>
Item [57], ABSTRACT,
Line 4, change "CRL-1771" to -- CRL-1711 --;

<u>Column 2,</u>
Line 37, change "CRL-1771" to -- CRL-1711 --;
Line 37, change "Sf-9" to -- CRL 1711 --;

<u>Column 8,</u>
Line 56, change "CRL-1771" to -- CRL-1711 --;
Line 56, change "Sf-9" to -- CRL 1711 --;

<u>Column 19,</u>
Line 26, change "CRL-1771" to -- CRL-1711 --;

<u>Column 20,</u>
Line 1, change "CRL-1771" to -- CRL-1711 --;
Line 11, change "Sf9" to -- CRL 1711 --;
Line 11, change "CRL-1771" to -- CRL-1711 --.

Signed and Sealed this

Sixteenth Day of May, 2006

JON W. DUDAS
*Director of the United States Patent and Trademark Office*